United States Patent [19]

Michel et al.

[11] Patent Number: 5,695,623

[45] Date of Patent: Dec. 9, 1997

[54] GLUCOSE MEASURING DEVICE

[75] Inventors: Peter Michel; Willy Michel, both of Burgdorf, Switzerland

[73] Assignee: Disetronic Licensing AG, Burgdorf, Switzerland

[21] Appl. No.: 656,135

[22] PCT Filed: Jun. 14, 1990

[86] PCT No.: PCT/CH90/00146

§ 371 Date: Jan. 25, 1994

§ 102(e) Date: Jan. 25, 1994

[87] PCT Pub. No.: WO91/00998

PCT Pub. Date: Jan. 24, 1991

[30] Foreign Application Priority Data

Jul. 7, 1989 [CH] Switzerland ............ 2535/89-7

[51] Int. Cl.$^6$ ........................................ G01N 27/26
[52] U.S. Cl. ..................... 204/403; 204/415; 204/406; 435/817; 435/287.1; 128/635
[58] Field of Search ............................ 204/403, 415, 204/406; 435/817, 288, 291; 128/635

[56] References Cited

U.S. PATENT DOCUMENTS 4,953,552  9/1990  De Marzo ................. 204/403
5,108,889  4/1992  Smith ....................... 204/403

*Primary Examiner*—Bruce F. Bell
*Attorney, Agent, or Firm*—McAulay Fisher Nissen Goldberg & Kiel, LLP

[57] ABSTRACT

The device for measuring and displaying the concentration of glucose in the blood comprises a display device (2) into which disposable sensors (1) comprising a biomembrane (9) can be inserted. The display device (2) comprises a built-in computer (3) in whose memory (7) a glucose concentration diagram (5) is stored and which can evaluate the measurement results of the sensors (1). The computer (3) comprises a time measuring device (4) whose zero setting can be correlated in an irreversible manner with the date of manufacture of the disposable sensors (1). Before the device is supplied to the patient, the glucose concentration diagram, which corresponds to the characteristics of the biomembrane (9) of the disposable sensors (1) at the time of manufacture, is irreversibly calibrated. The glucose concentration diagram is automatically and irreversibly corrected, taking into account the time-dependent characteristics of the biomembrane (9) of the disposable sensors (1), by means of the time measuring device (4).

20 Claims, 3 Drawing Sheets

GLUCOSE MEASURING DEVICE

BACKGROUND OF THE INVENTION

The invention is directed to a device for measuring and displaying the glucose concentration in the blood.

Such glucose measuring devices for diabetics are already known and substantially comprise the actual measuring device (glucometer) and exchangeable sensors (glucosensors) which can be inserted in the latter and on which a small quantity of the blood to be determined is placed. The blood required for this is removed by the user in a conventional manner by means of pricking the fingertip. When the sensor is inserted its biomembrane makes electrical contact with the measuring device, so that the changes in voltage and/or current of the active biomembrane of the sensor brought about by the different glucose contents are transmitted to the measuring device. The relevant measuring range of blood glucose in diabetics is between 4 and 15 mmol/l (=70–270 mg/dl). The measuring range of such devices is also typically 3–16 mmol/l (=50–300 mg/dl) so as to be able to measure in the clinical range as well.

The glucose measuring devices according to the prior art are too complicated, difficult to operate, unreliable and therefore also dangerous for the patient. In particular, it has been shown that the biomembrane of glucose sensors, whose active component consists of an unstable enzyme, e.g. glucose oxidase, is difficult to manufacture in a reproducible manner on the one hand and is subject to various changes in its characteristics caused by aging on the other hand.

SUMMARY OF THE INVENTION

The invention seeks to provide a remedy for this. The object of the invention is to provide a glucose measuring device by means of which it is possible to regulate all essential influencing variables already during the manufacture of the glucose measuring device by means of a unique calibration which cannot be altered for the patient while simultaneously taking into account the changes in the influencing variables caused by aging.

The invention meets this object by means of a glucose measuring device including disposable sensors comprising a biomembrane and a display device which can be calibrated and works on the basis of the glucose concentration diagram to evaluate the measurement results of the sensors. The display device comprises a computer with a time measuring device, whose zero setting can be correlated with the date of manufacture of the disposable sensors in an irreversible manner. An irreversible calibration of the glucose concentration diagram is provided which corresponds to the characteristics of the biomembrane of the disposable sensors at the time of their manufacture. At least one automatic and irreversible correction of the glucose concentration diagram which is influenced by the time measuring device is provided which takes into account the time-dependent characteristics of the biomembrane of the disposable sensors.

In practice, the glucose measuring device, according to the invention, is given to the patient as a complete package in the form of a display device (computer with time measuring device) together with 200–300 sensors. This quantity of sensors is generally sufficient for a half year to one whole year. The measuring and evaluating characteristics of the display device and disposable sensors, which characteristics are specifically adapted to one another, and the adaptation of the evaluating parameters to the aging-dependent measurement parameters of the sensors, which is made possible by means of the internal time measuring device of the display device, guarantees a high accuracy of the measuring results on the one hand and ensures a high degree of safety in operation on the other hand.

The advantages achieved by means of the invention substantially consist in that it is no longer necessary to calibrate the device to the disposable sensors which are to be contacted, specifically neither a first calibration when starting operation, nor a secondary calibration during the life of the device is necessary as a result of the glucose measuring device, according to the invention. As a result of the automatic correction of all important parameters and the preferable limitation of the life of the device, no maintenance is necessary.

In a preferred embodiment form of the device, according to the invention, the glucose concentration diagram, which can be a function of the measurement current as well as of the measurement voltage, is determined by means of a one-point or multiple-point calibration. The calibration can be effected by way of hardware, e.g. by means of trimming in the analog part (calibration), or also by way of software, e.g. by means of a table in the arithmetic memory. It allows a calibration on the part of the manufacturer which is accurately adapted to the disposable sensors provided along with the display device and originating from a single production batch and which rules out errors on the part of the patient in this exacting operation.

In a preferred embodiment form of the device, according to the invention, the ends of the sensor and display device, which face one another and can be coupled, comprise corresponding cams and grooves. The exact shape and arrangement of these key/lock elements is modified periodically in the manufacturing of the sensors and display devices, so that sensors from previous production batches—in which the enzyme immobilized on the biomembrane has a weakened reaction sensitivity as a result of aging—can no longer be used with the display devices from the recent production batches. A further source of error and danger on the part of the patient can accordingly be ruled out to a great extent.

As an alternative to this key/lock safety device, it is also possible to provide the sensors with a bar code which can be read only by a display device which is authorized for these sensors.

In another preferred embodiment form of the device, according to the invention, an additional temperature sensor is provided, which is preferably arranged in the immediate vicinity of the biomembrane of the sensor and takes into account the dependence of the glucose concentration diagram on temperature.

In so doing, the supplied sensors are advisably preserved in a drawer (cartridge) provided in the display device; the temperature sensor opens into this drawer. Fluctuations in temperature, which can easily range from 15°–25° C., are accordingly taken into account, which leads to a considerably more reliable measurement of the glucose values.

In sensors according to the prior art, the shelf life is limited to approximately one year; therefore, in another preferred embodiment form of the device, according to the invention, the computer is pre-programmed in such a way that the device is automatically and irreversibly switched off and made inoperative after a predetermined service life or number of measurements. This function can be easily realized with the existing internal time measurement device and is of an importance which is not to be underestimated. Limiting the life of the glucose measuring device prevents the use of sensors which are too old and accordingly no longer able to measure in a reliable manner. The patient is accordingly compelled to have a new device given to him by the doctor with new sensors adapted to it, which once again ensures a faultless and reliable determination of the blood glucose values. The life of the energy-supplying batteries should advisably be adapted to the life of the device which is pre-programmed in this way, so that a change of batteries is also unnecessary.

The computer is advisably pre-programmed in the device, according to the invention, in such a way that the automatic and irreversible correction of the glucose concentration diagram, which is influenced by the time measuring device and takes into account the time-dependent characteristics of the disposable sensors, is effected by means of a batch-dependent reaction sensitivity diagram. Accordingly, it is possible to take into account the reaction sensitivity of the enzyme immobilized on the biomembrane of the sensor, e.g. glucose oxidase, which reaction sensitivity generally decreases with increasing age. The decrease in activity responds in initial approximation to a decreasing e-function which can be stored in the computer in the form of a program or a table.

In another preferred embodiment form of the device, according to the invention, it is provided that the computer comprises a memory which can store the measured blood glucose values for subsequent evaluations. This makes it possible e.g. to replay the glucose values of an entire measurement period (30–50 measurement values) in an external device (e.g. personal computer) where they can be reprocessed and evaluated in order to reinforce therapy.

The internal clock is designed in such a way that the patient cannot set it himself. If required, it can be regulated externally by the doctor. However, the time is only of interest in relation to the stored measurement values for the blood glucose content, so that the clock adjustment can advisably be effected when reading out the values.

An embodiment example of the invention which simultaneously explains the principle of operation is shown in the drawing and described in more detail in the following.

DESCRIPTION OF THE PREFERRED EMBODIMENT

Figure 1:
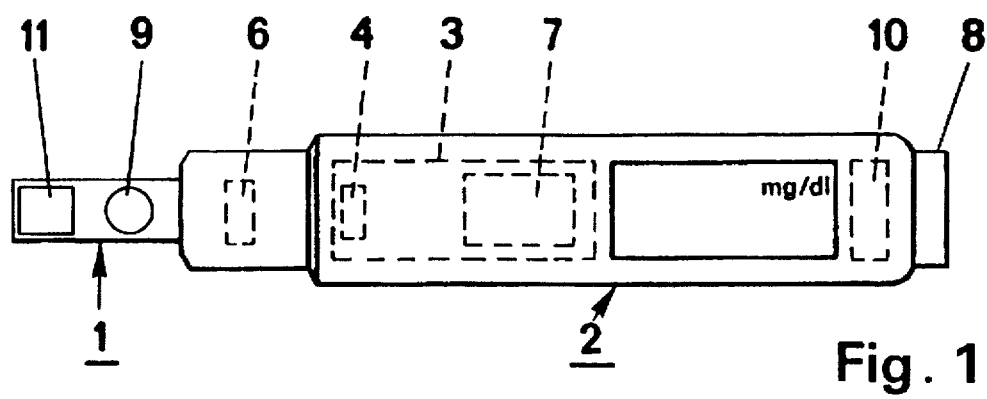
FIG. 1 shows a schematic general view of the measuring device with inserted measurement strip.

The measuring device 2 shown in the measuring state in FIG. 1 with inserted sensor 1 substantially comprises a computer 3 with an internal clock 4 and a memory 7, a temperature sensor 6, a battery 10, and a push button 8 which sets all functions of the device in operation.

Figure 2:
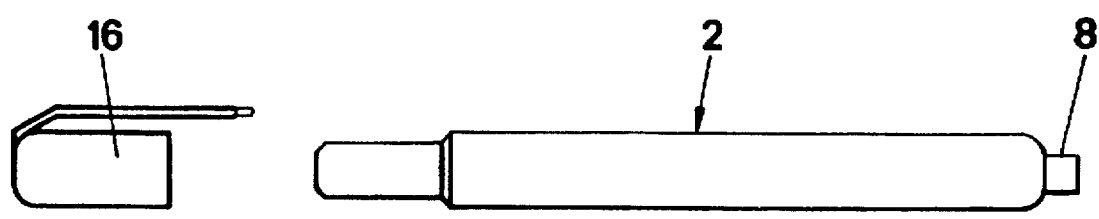
FIG. 2 shows a side view of the measuring device with closing cap.

The end of the device 2 determined for plug-in contact with the sensor 1 is in the rest state, as shown in FIG. 2, with closed attachment clip 16, which simultaneously serves as a cartridge for the sensors 1 which have not yet been used.

This has the advantage that the temperature sensor 6 measures a value coming as close as possible to the actual temperature of the sensor 1 and transmits it to the computer 3.

Figure 3:
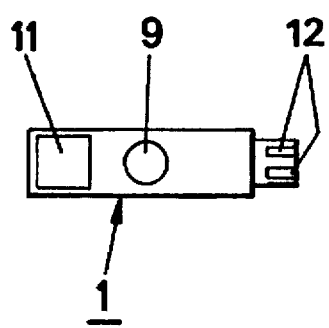
FIG. 3 shows a top view of a sensor.
Figure 4:
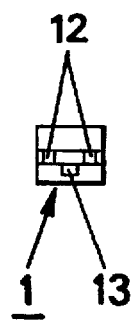
FIG. 4 shows a front view of the sensor.
Figure 5:
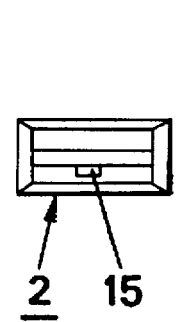
FIG. 5 shows a front view of the display device.

The sensor 1, which is shown in detail in FIGS. 1, 3 and 4, comprises an elongated strip of plastic which comprises the electrical contacts 12 for the connection with the display device 2 at one end and a handle surface 11 for manipulating it (insertion and removal) at the other end. The biomembrane 9, on which the drops of blood to be measured are to be placed, is arranged in the center of the sensor 1. The biomembrane 9 comprises an amperometric electrode with an enzyme membrane comprising glucose oxidase. A cam 13, which fits into a corresponding groove 15 of the end of the display device 2 on the insertion end, is attached to the end of the sensor 1 on the insertion end between the electrical contacts 12 (FIG. 5).

The exact shape and arrangement of these key/lock elements 13, 15 is advisably changed every 6 to 12 months in the manufacturing of the sensors 1 and display devices 2, so that sensors 1 of earlier production batches—with a weakened reaction sensitivity of the glucose oxidase due to aging—can no longer be used with the display devices 2 from the recent production batches. As an alternative to this key/lock safety device 13, 15, it is also possible to provide the sensors 1 with a bar code which can be read only by a display device 2 authorized for use with these sensors 1.

Figure 6:
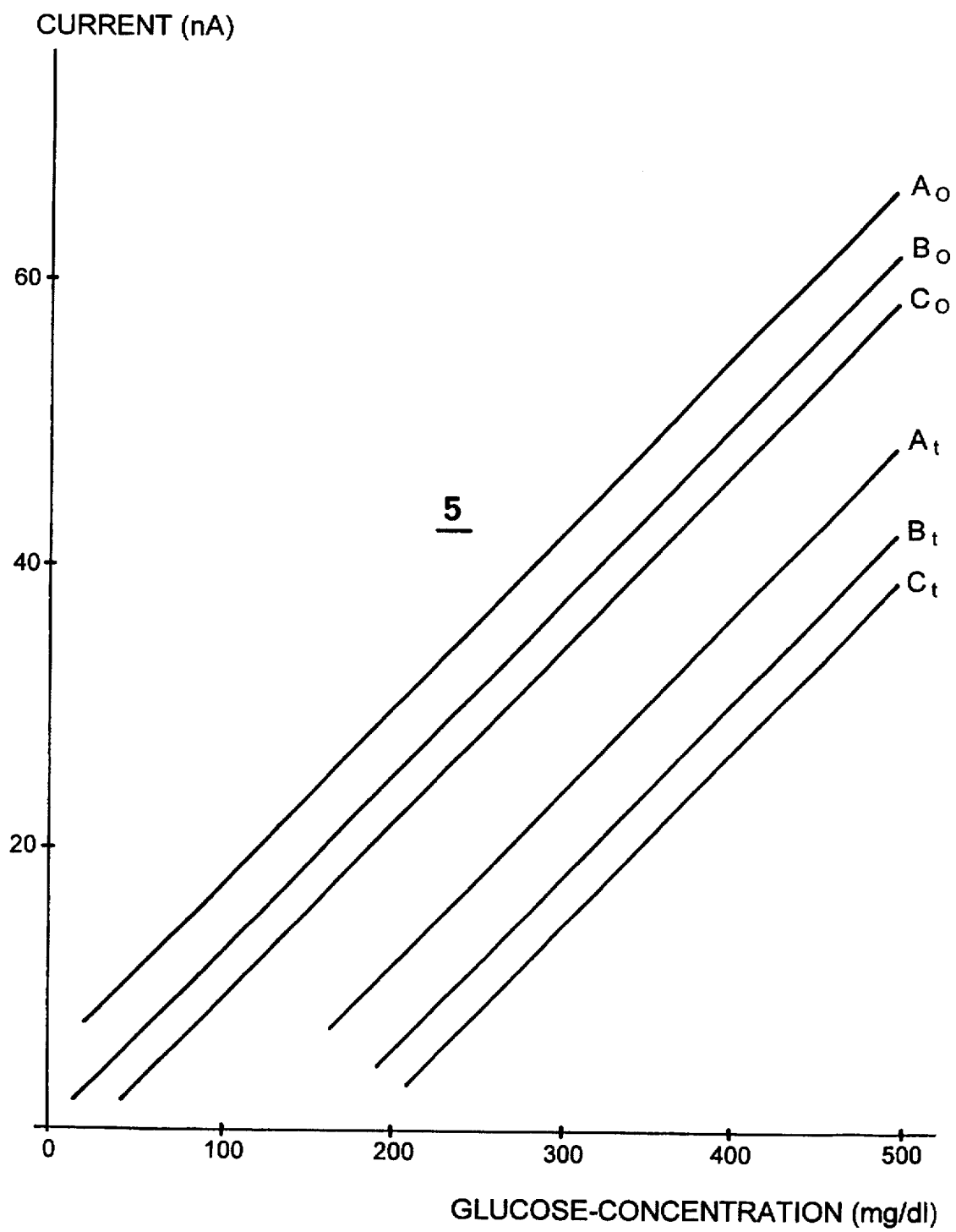
FIG. 6 shows a diagram of glucose concentration/ measurement current with different batch-dependent curves and their dependence on aging.

Prior to supplying the display device 2 to the patient or to trade, this display device 2 is calibrated by the manufacturer to the sensors 1 which are to be simultaneously supplied with it, i.e. the zero setting of the computer 3 is correlated with the date of manufacture of the disposable sensors 1 in a manner which cannot be altered for the patient. As is shown in FIG. 6, the glucose concentration diagram 5 consists of a number of charge-dependent curves $A_0$, $B_0$, $C_0$ (valid for time point t=0, i.e. the time of the manufacture of the sensors 1). Depending on the production batch, the enzyme (e.g. glucose oxidase) which is immobilized on the biomembrane 9 of the sensor 1 shows a greater or lesser degree of activity (batch A: calibration curve $A_0$/ batch B: calibration curve $B_0$/ batch C: calibration curve $C_0$). As a rule, the batch-dependent glucose calibration curve $A_0$, $B_0$, $C_0$ is linear and has a constant slope in initial approximation. Accordingly, a one-point calibration is generally sufficient for the calibrating process. For more complicated calibration curves, such as could exist when using other enzymes, a two-point or multiple-point calibration would be necessary.

With this first or zero calibration, the memory 7 of the computer possesses the glucose concentration diagram 5 valid at the time point t=0 of the manufacture of a determined batch of sensors 1, e.g. $C_0$ (corresponding to the sensors of batch C which were supplied), for a selected mean normal temperature.

Figure 7:
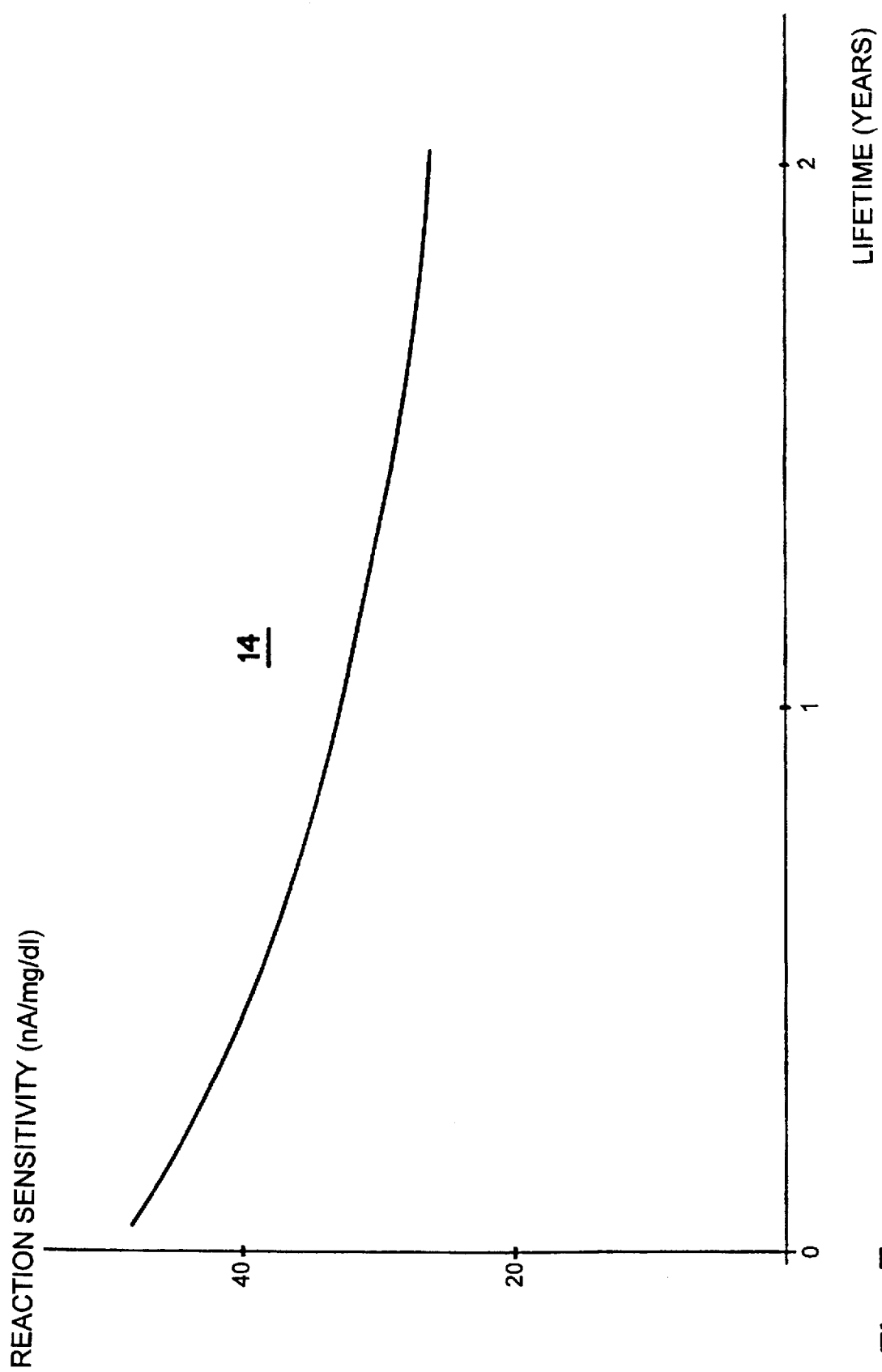
FIG. 7 shows a reaction sensitivity diagram.

As a result of the aging of the utilized enzyme, there is a decrease in activity of the enzyme as the age progresses, as shown in FIG. 7, which is manifested in the glucose concentration diagram 5 (FIG. 6) by means of a downward shifting of the calibration curves $A_0$, $B_0$, $C_0$ ($A_t$, $B_t$, $C_t$). The computer 3 can carry out a determination of the respective valid glucose calibration curve, e.g. $C_t$ (for sensors of batch C and age t) automatically and without the influence of the patient so as to take into account the time-dependent characteristics of the biomembrane 9 of the disposable sensors 1 by means of the internal clock 4 and the glucose concentration diagram 5 and enzyme reaction sensitivity diagram 14 present in the memory 7.

All of the calibration curves shown in FIG. 6 are calculated for a determined mean normal temperature. Since the reaction sensitivity of the enzyme immobilized on the biomembrane 9 is dependent on the temperature, it is advisable to carry out a temperature correction. The temperature coefficient varies for the individual enzymes and amounts to approximately 5%/°C. (at a concentration of 20 mmol/l) for the glucose oxidase which is preferably used, wherein the reaction sensitivity increases as the temperature increases, i.e. changes in the same direction. In addition to the valid curve $C_t$ for a selected normal temperature (for sensors of batch C and age t), curves which are derived from the latter and are a function of the temperature actually measured by the temperature sensor 6 are accordingly stored in the memory 7 of the computer 3.

We claim:

1. A device for measuring and displaying the glucose concentration in the blood by means of disposable sensors comprising a biomembrane and a display device which works on the basis of the glucose concentration diagram and evaluates the measurement results of the sensors, the display device having a calibration means wherein:

A) the display device comprises a computer with a time measuring device, whose zero setting is correlated with the date of manufacture of the disposable sensors in an irreversible B) an irreversible calibration of the glucose concentration diagram is provided which corresponds to the characteristics of the biomembrane of the disposable sensors at the time of their manufacture;

C) at least one automatic and irreversible correction of the glucose concentration diagram which is influenced by the time measuring device is provided which takes into account the time-dependent characteristics of the biomembrane of the disposable sensors.

2. The device according to claim 1, wherein the display device is responsive to a multiple-point calibration of the glucose concentration diagram.

3. The device according to claim 2, wherein a temperature sensor is provided, which takes into account the dependence of the glucose diagram on temperature.

4. The device according to claim 3, wherein the computer is preprogrammed to automatically and irreversibly switch off and make inoperative the device after a set service life or number of measurements.

5. The device according to claim 4, wherein the computer comprises a memory by means of which the measured blood glucose values for subsequent evaluations can be stored.

6. The device according to claim 5, wherein all functions of the device are triggered by means of a single push button.

7. The device according to claim 6, wherein the sensor comprises an amperometric electrode with an enzyme membrane.

8. The device according to claim 7, wherein the display device is responsive to a calibration of the glucose concentration diagram relating glucose concentration as a function of the measurement current.

9. The device according to claim 8, wherein the computer is preprogrammed to effect, by means or a batch-dependent reaction sensitivity diagram, the automatic and irreversible correction of the glucose concentration diagram, which is influenced by the time measuring device and takes into account the time-dependent characteristics of the disposable sensors.

10. The device according to claim 9, wherein the ends of the sensor and display device, which face one another and are coupleable with one another, comprise key/lock elements which correspond with one another.

11. The device according to claim 1, wherein the computer is preprogrammed to automatically and irreversibly switch off and make inoperative the device after a set service life or number of measurements.

12. The device according to claim 1, wherein the computer comprises a memory by means of which the measured blood glucose values for subsequent evaluations can be stored.

13. The device according to claim 1, wherein all functions of the device are triggered by means of a single push button.

14. The device according to claim 1, wherein the sensor comprises an amperometric electrode with an enzyme membrane.

15. The device of claim 14, wherein the enzyme membrane is a glucose oxidase membrane.

16. The device according to claim 1, wherein the display device is responsive to a calibration of the glucose concentration diagram relating glucose concentration as a function of the measurement current.

17. The device according to claim 1, wherein the computer is preprogrammed to effect, by means of a batch-dependent reaction sensitivity diagram the automatic and irreversible correction of the glucose concentration diagram, which is influenced by the time measuring device and takes into account the time-dependent characteristics of the disposable sensors.

18. The device according to claim 1, wherein the ends of the sensor and display device, which face one another and are coupleable with one another, comprise key/lock elements which correspond with one another.

19. The device according to claim 18 wherein the key/lock elements are in the form of cams aid grooves.

20. The device according to claim 1, wherein a temperature sensor is provided, which takes into account the dependence of the glucose diagram on temperature.

* * * * *